United States Patent [19]

Lemole

[11] Patent Number: 4,535,770
[45] Date of Patent: Aug. 20, 1985

[54] CARDIOVASCULAR TOURNIQUET

[76] Inventor: Gerald M. Lemole, 404 Tomlinson Rd., Huntingdon Valley, Pa. 19046

[21] Appl. No.: 547,985

[22] Filed: Nov. 2, 1983

[51] Int. Cl.³ ............................................ A61M 25/02
[52] U.S. Cl. .................................... 128/327; 604/239; 604/264
[58] Field of Search ....... 128/327, 346, 335, DIG. 26; 604/239, 240, 241, 264, 272, 278, 280; 24/3 J, 3

[56] References Cited

U.S. PATENT DOCUMENTS

| | | | |
|---|---|---|---|
| 3,043,308 | 7/1962 | Seltzer | 128/327 |
| 3,476,114 | 11/1969 | Shannon et al. | 128/346 |
| 3,507,270 | 4/1970 | Ferrier | 128/327 |
| 3,769,663 | 11/1973 | Perl | 24/3 J |
| 3,877,434 | 4/1975 | Ferguson et al. | 128/327 |
| 4,002,174 | 1/1977 | Reed et al. | 604/272 |
| 4,167,946 | 9/1979 | Sandstrom | 128/DIG. 26 |
| 4,291,698 | 9/1981 | Fuch | 128/335 |

FOREIGN PATENT DOCUMENTS 301415  10/1917  Fed. Rep. of Germany ... 128/DIG. 26

Primary Examiner—Gene Mancene
Assistant Examiner—John G. Weiss
Attorney, Agent, or Firm—Robert J. Mooney

[57] ABSTRACT

A cardiovascular tourniquet and surgical method of applying the same is disclosed for use in support of a cannula operatively inserted into a blood vessel with a purse string suture. Ends of the suture are drawn to close the blood vessel around the cannula and then passed through a tubular member having integrally formed rib-like sections spaced apart along its length. The tubular member is firmly secured alongside the cannula by at least a pair of spring clips fastened about the cannula and adapted to grasp the tubular member between its rib-like sections. An integral cap is further provided at one end of the tubular member for releasably clamping the suture ends drawn therethrough thereby preventing the suture from loosening during subsequent procedures and maintaining proper disposition of the cannula.

8 Claims, 4 Drawing Figures

CARDIOVASCULAR TOURNIQUET

BACKGROUND OF THE INVENTION

The present invention relates to cardiovascular surgical procedures, and more particularly to an improved means and associated method for applying a tourniquet in support of a cannula operatively inserted into a blood vessel.

During major surgical procedures, particularly those treating the cardiovascular system, a fluid connection with a closed blood vessel is often required and is typically effected by insertion of a sharply pointed tube, known as a cannula, into the vessel. The cannula is properly fed through an opening surgically formed in the wall of the blood vessel and about which is provided a "purse string" suture for closing the opening around the cannula so that a substantially fluid-tight seal is permitted.

To provide support to the cannula and maintain its substantially fluid tight seal within the blood vessel, the ends of the suture are often passed through a length of smooth flexible tubing, commonly referred to as a tourniquet. Firmly positioned along side of the cannula, usually by lashing, such a tubular tourniquet has heretofore required the ends of the suture, which are drawn tightly therethrough, to be releasably clamped at the far end of the tourniquet length using separate clamping devices, such as forceps, to prevent the suture from loosening during subsequent procedures. While generally providing adequate sealed support for the cannula inserted within the blood vessel, this current surgical method, using the described tourniquet with the required lashing and separate clamping, consumes a significant and undesirable amount of time, and as a result, increases the risk of serious trauma occuring during the surgery.

SUMMARY OF THE INVENTION

Accordingly, it is the general purpose and object of the present invention to provide an improved means and associated method for producing a firm fluid-tight connection between a cannula and a designated blood vessel during surgery.

A more particular object of the present invention is to provide a surgical apparatus and procedure for applying an effective tourniquet at the joint between a cannula and a blood vessel, such as an artery, in a reduced period of time.

A further object of the present invention is to provide a surgical technique of applying an arterial tourniquet in support of a cannula that is safe and easy to implement manually, reliable in its performance, and easily adapted to existing cardiovascular surgical operations.

Briefly, these and other objects of the present invention are accomplished by a cardiovascular tourniquet and surgical method of applying the same for use in support of a cannula operatively inserted into a blood vessel with a purse string suture. The ends of the suture are drawn to close the blood vessel around the cannula and then passed through a tubular member having integrally formed rib-like sections spaced apart along its length. The tubular member is firmly secured along the length of the cannula by at least a pair of spring clips fastened about the cannula and adapted to grasp the tubular member between its rib-like sections. An integral cap is further provided at one end of the tubular member for releasably clamping the suture ends drawn therethrough thereby preventing the suture from loosening during subsequent procedures and maintaining proper disposition of the cannula.

For a better understanding of these and other aspects of the present invention, reference may be made to the following detailed description taken in conjunction with the accompanying drawings in which like reference numerals designate like parts throughout the figures thereof.

DESCRIPTION OF THE PREFERRED EMBODIMENT

Figure 1:
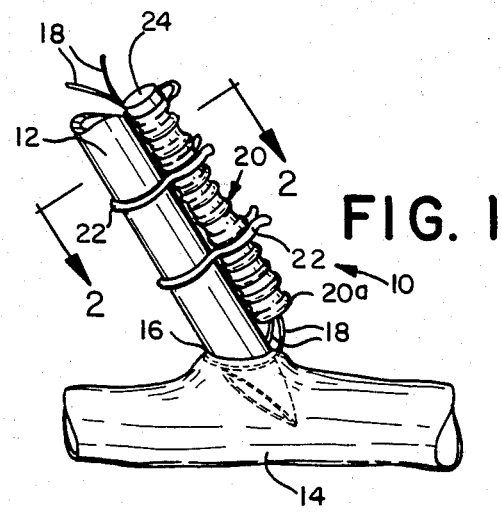
FIG. 1 is an enlarged perspective view of a typical cannula inserted into a blood vessel, showing the application of a cardiovascular tourniquet in accordance with the present invention.

Referring now to FIG. 1, there is shown the cardiovascular tourniquet 10 of the present invention applied in support of a surgical steel cannula 12 that is surgically inserted into a blood vessel 14 for conveying blood to or from the vessel. Cannula 12 is typically inserted into the blood vessel 14, such as an artery, through an opening 16 surgically formed in the wall of the vessel, the opening being provided with a purse-string or like suture 18 for closing the walls of the vessel about the cannula thereby forming a sealable, substantially fluid-tight connection therebetween.

According to the present invention, tourniquet 10 comprises a tubular member 20 fabricated from a relatively flexible material such as silicone or natural rubber or the like, that is formed in a substantially cylindrical configuration having a plurality of rib-like sections 20a transversely disposed upon its outer surface. Protruding radially from the basic outer diameter of tubular member 20, the rib-like sections 20a are spaced apart along the length of the tubular member by substantially equal distances. Tubular member 20 is further provided at one end thereof with a removable cap 24, preferably integrally formed and described in greater detail hereinafter in reference to FIGS. 3A and 3B.

Figure 2:
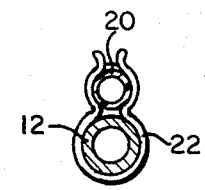
FIG. 2 is a sectional view of the applied tourniquet shown in FIG. 1 taken along the line 2—2.

Referring now to FIG. 2 in conjunction with FIG. 1, tourniquet 10 further comprises at least a pair of spring clips 22 that may be fabricated from a plastic with memory such as FDA approved Delrin or the like. Each spring clip 22 is formed having a dual ring-like configuration as shown in FIG. 2, conforming to the outer diameters of the cylindrical surface of cannula 12 and tubular member 20. Adapted at one end to be closed about and fastened to the outer surface of cannula 12, each spring clip 22 is bifurcated and slightly open at the opposite end to permit transverse gripping engagement of tubular member 20. The spring clips 22 are separated and positioned along the cannula 12 so that each spring clip engages the tubular member 20 between a set of adjacent rib-like sections 20a thereby firmly grasping the tubular member about its basic outer diameter and preventing relative motion between the member and the cannula during subsequent surgical procedures. It should be noted that the use of one spring clip 22 is effective in grasping tubular member 20 and holding it substantially alongside cannula 12 without significant longitudinal movement of the member. However, use of at least a pair of clips 22 is preferred to prevent further movement of tubular member 20, particularly rotational shifting or twisting of the member 20 upon cannula 12 that may occur during subsequent procedures.

Figure 3A:
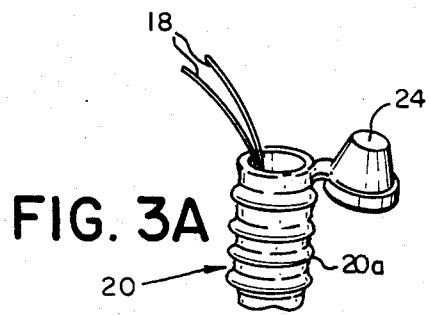
FIGS. 3A and 3B are partial views of the tourniquet of FIGS. 1 and 2, more closely showing the clamping feature of its integral cap in open and closed positions, respectively.
Figure 3B:
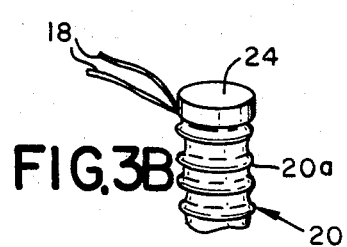

Referring now to FIGS. 3A and 3B in conjunction with FIG. 1, cap 24 is integrally formed at one end of tubular member 20, the cap preferably being tethered a short distance from the end to permit free movement of the cap into and out of the tubular member while remaining in close proximity thereto. The body of cap 24 is wedge-like in form, typically being a truncated cone as shown in FIG. 3A, and is made having sufficient cross-sectional size so that, when fully inserted within the end of tubular member 20, as shown in FIG. 3B, the cap fits tightly therein, providing firm clamping action upon suture ends 18 passed therethrough.

With reference now to all the drawing figures, the operation and method of applying the cardiovascular tourniquet 10 may be explained. After insertion of cannula 12 into blood vessel 14 through annular opening 16, purse string suture 18 is drawn tightly to close the walls of the vessel around the cannula and then passed through tubular member 20, the ends of the suture being inserted at the end of the tubular member opposite cap 24. With the ends of the suture 18 held firmly, tubular member 20 is moved alongside cannula 12 and quickly secured thereto by engagement with the open ends of the spring clips 22 fastened about the cannula. Engaged by the spring clips 22 between sets of adjacent rib-like sections 20a formed therealong, tubular member 20 is thus intimately secured to cannula 12 and prevented from moving relative thereto. With the tubular member 20 thus firmly in place, cap 24 is fully inserted into the proximal end of the member to clamp the ends of the drawn suture 18 thereby preventing the suture 18 from loosening during subsequent procedures and maintaining the proper disposition of cannula 12 in blood vessel 14.

The disclosed invention provides an improved surgical means and associated method for producing a firm, fluid-tight connection between a cannula and a blood vessel, particularly providing a surgical apparatus and procedure for applying an effective and secure tourniquet at the joint between the cannula and the blood vessel, such as an artery, in a reduced period of time. In addition, the disclosed cardiovascular tourniquet and method for applying the same in support of an operatively-inserted cannula is safe and easy to implement manually, reliable in its performance, and easily adapted to existing cardiovascular surgical operations.

Obviously, other embodiments and modifications of the present invention will readily come to those of ordinary skill in the art having the benefit of the teachings presented in the foregoing description and drawings. It is therefore to be understood that various changes in the details, materials and steps, and arrangement of parts, which have been described and illustrated to explain the nature of the invention, may be made by those skilled in the art within the principle and scope of the invention as expressed in the appended claims.

I claim:

1. A tourniquet for use in support of a cannula operatively inserted into a blood vessel comprising:
   a tubular member;
   a plurality of protruding members disposed about the outer surface of said tubular member and separated along its length; and
   a plurality of clip members adapted to be fastened about the cannula and disposed to engage said tubular member between said protruding members.

2. A tourniquet according to claim 1, wherein said protruding members comprise:
   rib-like sections integrally formed about said tubular member and spaced apart therealong by substantially equal distances.

3. A tourniquet according to claim 1, further including a cap integrally formed with and tethered to said tubular member.

4. A tourniquet according to claim 3, wherein said cap is in the form of a truncated cone.

5. A tourniquet according to claim 1, wherein:
   said clip members are bifurcated and slightly open to permit transverse engagement of said tubular member.

6. A tourniquet for use in support of a cannula operatively inserted into a blood vessel comprising:
   a tubular member;
   a plurality of rib-like sections integrally formed to protrude radially about said tubular member at separate positions along its length;
   a cap integrally formed and tethered to said tubular member at one end thereof for removable insertion therein; and
   a plurality of clip members adapted to be fastened about the cannula and disposed to engage said tubular member between said rib-like sections.

7. A tourniquet according to claim 6, wherein:
   said clip members are formed having a dual ring-like configuration, bifurcated and slightly open at one end to permit transverse engagement of said tubular member.

8. A method of applying a tourniquet in support of a cannula operatively inserted into a blood vessel and secured thereto with a purse string suture, comprising the steps of:
   drawing the suture tightly to close the vessel around the cannula;
   passing the ends of the suture through a tubular member having rib-like sections along its length;
   securing the tubular member alongside the cannula with clips fastened about the cannula and disposed to engage the tubular member between adjacent rib-like sections; and
   clamping the ends of the drawn suture passed through the end of the tubular member with a cap tethered thereto.

* * * * *